US012119019B2

(12) United States Patent
Maclaren et al.

(10) Patent No.: US 12,119,019 B2
(45) Date of Patent: Oct. 15, 2024

(54) PRIVACY-PRESERVING SOCIAL INTERACTION MEASUREMENT

(71) Applicant: Google LLC, Mountain View, CA (US)

(72) Inventors: Julian Maclaren, Nelson (NZ); Karolis Misiunas, Zurich (CH); Vahe Tshitoyan, Pleasanton, CA (US); Brian Foo, Union City, CA (US); Kelly Dobson, Santa Cruz, CA (US)

(73) Assignee: Google LLC, Mountain View, CA (US)

( * ) Notice: Subject to any disclaimer, the term of this patent is extended or adjusted under 35 U.S.C. 154(b) by 334 days.

(21) Appl. No.: 17/578,217

(22) Filed: Jan. 18, 2022

(65) Prior Publication Data

US 2023/0230612 A1    Jul. 20, 2023

(51) Int. Cl.
| | |
|---|---|
| *G10L 25/51* | (2013.01) |
| *A61B 5/024* | (2006.01) |
| *G10L 15/22* | (2006.01) |
| *G10L 21/028* | (2013.01) |
| *G10L 25/78* | (2013.01) |
| *H04R 1/04* | (2006.01) |
| *H04R 1/40* | (2006.01) |
| *H04R 3/00* | (2006.01) |

(52) U.S. Cl.
CPC .......... *G10L 25/51* (2013.01); *A61B 5/02416* (2013.01); *G10L 15/22* (2013.01); *G10L 21/028* (2013.01); *G10L 25/78* (2013.01); *H04R 1/04* (2013.01); *H04R 1/406* (2013.01); *H04R 3/005* (2013.01); *A61B 2503/12* (2013.01)

(58) Field of Classification Search
CPC ....... G10L 25/51; G10L 15/22; G10L 21/028; G10L 25/78; A61B 5/02416; A61B 2503/12; H04R 1/04; H04R 1/406; H04R 3/005
See application file for complete search history.

(56) References Cited

U.S. PATENT DOCUMENTS

| | | | |
|---|---|---|---|
| 2015/0310857 A1* | 10/2015 | Habets | G10L 15/14 704/240 |
| 2018/0042542 A1* | 2/2018 | Cronin | A61B 5/4803 |
| 2019/0043512 A1* | 2/2019 | Huang | G10L 17/26 |
| 2019/0336080 A1* | 11/2019 | LeBoeuf | A61B 5/7275 |
| 2021/0015415 A1* | 1/2021 | Ofir | A61B 5/1118 |
| 2022/0076680 A1* | 3/2022 | Wexler | G10L 15/22 |
| 2023/0239800 A1* | 7/2023 | Wang | G10L 15/22 370/311 |

FOREIGN PATENT DOCUMENTS

WO    WO-2020027771 A1 *    2/2020    ......... G06F 16/685

* cited by examiner

*Primary Examiner* — Sonia L Gay (74) *Attorney, Agent, or Firm* — Kilpatrick Townsend & Stockton LLP (57) ABSTRACT

Various systems, devices, and methods for social interaction measurement that preserve privacy are presented. An audio signal can be captured using a microphone. The audio signal can be processed using an audio-based machine learning model that is trained to detect the presence of speech. The audio signal can be discarded such that content of the audio signal is not stored after the audio signal is processed using the machine learning model. An indication of whether speech is present within the audio signal can be output based at least in part on processing the audio signal using the audio-based machine learning model.

14 Claims, 7 Drawing Sheets

PRIVACY-PRESERVING SOCIAL INTERACTION MEASUREMENT

BACKGROUND

Modern life can allow a person to conduct their day-to-day lives with little to no spoken interaction with others. Factors that can also lead to isolation can include: remote working, delivery services, social media, and pandemics. However, person-to-person communication, and especially face-to-face communication, in which at least two people are physically in proximity talking to each other, can have significant mental health benefits. While previously people may have had a significant amount of face-to-face contact with other people, both friends and strangers, on a day-to-day basis simply by going about their lives, modern life does not necessarily provide such opportunities. A person may desire to understand how much social interaction they are getting and perhaps modify their lifestyle in view of such an understanding.

SUMMARY

Various embodiments are described related to a wearable device. In some embodiments, a wearable device is described. The device may comprise a housing. The device may comprise an attachment mechanism, attached with the housing, that may permit the wearable device to be worn by a wearer. The device may comprise a microphone housed by the housing. The device may comprise a processing system comprising at least one processor, communicatively coupled with the microphone and housed by the housing. The processing system may be configured to receive an audio signal from the microphone. The processing system may be configured to process the audio signal using an audio-based machine learning model stored by the processing system. The audio-based machine learning model may be trained to detect a presence of speech. The processing system may be configured to output an indication of whether speech may be present within the audio signal based at least in part on processing the audio signal using the audio-based machine learning model. The processing system may be configured to discard the audio signal such that the audio signal may not be stored after the indication of whether speech is present is output.

Embodiments of such a device may include one or more of the following features: the device may further comprise a photoplethysmography (PPG) sensor, housed by the housing and in communication with the processing system, that may output a PPG signal to the processing system. The processing system may be further configured to process the PPG signal received from the PPG sensor using a PPG-based machine learning model stored by the processing system. The processing system may be further configured to, using a first output of the audio-based machine learning model and a second output of the PPG-based machine learning model, determine whether the audio signal may comprise speech spoken by the wearer of the wearable device. The indication of whether speech is present may be indicative of whether speech spoken by the wearer is present. The processing system may be further configured to process a first output of the audio-based machine learning model and a second output of the PPG-based machine learning model using a second-level machine learning model. The second-level machine learning model may output the indication of whether speech is present. The indication of whether speech is present may be indicative of whether speech spoken by the wearer is present. The device may further comprise a plurality of microphones, that may comprise the microphone, in communication with the processing system and the processing system. The device may further comprise the processing system that may be further configured to process a plurality of audio streams from the plurality of microphones using a directionality analyzer. The second-level machine learning model may further use a third output from the directionality analyzer. The indication of whether speech is present may be further indicative of whether the wearer is participating in a person-to-person conversation. The device may further comprise an inertial measurement unit (IMU), housed by the housing and in communication with the processing system, that may output an inertial signal to the processing system. The processing system may be further configured to process the inertial signal received from the IMU using an inertial-based machine learning model stored by the processing system. The processing system may be further configured to using a first output of the audio-based machine learning model, a second output of the PPG-based machine learning model, and a third output of the inertial-based machine learning model, determine whether the audio signal may comprise speech spoken by the wearer of the wearable device. The indication of whether speech is present may be indicative of whether speech spoken by the wearer is present. The attachment mechanism may comprise a band that permits the wearable device to be worn on a wrist of the wearer. The wearable device may be a smartwatch that may further comprise a graphical electronic display, housed by the housing and in communication with the processing system. The wearable device may be a smartwatch that may further comprise a wireless communication interface, housed by the housing and in communication with the processing system that enables the processing system to communicate wirelessly with a smartphone. The processing system may be further configured to calculate an amount of time in a day that the wearer may be socially engaged based at least on the indication of whether speech is present within the audio signal. The processing system may be further configured to cause the amount of time in the day that the wearer may be socially engaged to be output to the wearer. The audio signal from the microphone may be only input to the audio-based machine learning model. The processing system may be further configured to perform a signal separation analysis on a plurality of audio signals received from a plurality of microphones of the wearable device. An output of the signal separation analysis may be an indication of a number of audio sources.

In some embodiments, a method for social interaction measurement is described. The method may comprise capturing, by a microphone of a wearable device, an audio signal. The method may comprise processing, by a processing system of the wearable device, the audio signal using an audio-based machine learning model. The audio-based machine learning model may be trained to detect a presence of speech. The method may comprise discarding, by the wearable device, the audio signal such that content of the audio signal is not stored after the audio signal is processed using the audio-based machine learning model. The method may comprise outputting, by the processing system, an indication of whether speech may be present within the audio signal based at least in part on processing the audio signal using the audio-based machine learning model.

Embodiments of such a method may include one or more of the following features: capturing photoplethysmography (PPG) data using a PPG sensor of the wearable device. The method may further comprise processing the PPG data received from the PPG sensor using a PPG-based machine learning model stored by the processing system. The PPG-based machine learning model may be trained to detect the presence of speech based on the PPG data. The method may further comprise using a first output of the audio-based machine learning model and a second output of the PPG-based machine learning model, determine whether the audio signal may comprise speech spoken by a wearer of the wearable device. The indication of whether speech is present may be indicative of whether speech spoken by the wearer is present. The method may further comprise processing a first output of the audio-based machine learning model and a second output of the PPG-based machine learning model using a second-level machine learning model. The second-level machine learning model may output the indication of whether speech is present. The indication of whether speech is present may be indicative of whether speech spoken by a wearer is present. Capturing the audio signal may comprise capturing a plurality of audio signals using a plurality of microphones of the wearable device. The method may further comprise performing a signal separation analysis on the plurality of audio signals received from the plurality of microphones of the wearable device. An output of the signal separation analysis may be an indication of a number of audio sources. The method may further comprise processing a plurality of audio streams from the plurality of microphones using a directionality analyzer. The second-level machine learning model may further use a third output from the directionality analyzer. The indication of whether speech is present may be further indicative of whether the wearer is participating in a face-to-face conversation.

BRIEF DESCRIPTION OF THE DRAWINGS

A further understanding of the nature and advantages of various embodiments may be realized by reference to the following figures. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

Research indicates that social interactions are important to a person's long-term mental well-being. Specifically, social isolation has been linked to poorer health, depression, and increased risk of an early death. However, measurement of social interactions can present significant privacy concerns. To measure a social interaction, it can be helpful to determine when a person is speaking. However, a person, rightfully, may not desire their speech, or the speech of those around them, to be recorded. This concern may be particularly acute when a device to measure social interactions is worn. Embodiments detailed herein are focused on measuring social interactions at least partly based on a person's speech, but doing so without storage of any speech or any data indicative of the content of such speech. Therefore, while the presence of speech may be detected and quantified, the content of the speech is never analyzed, recorded, transmitted by the device, or stored.

In some embodiments, a wearable device can be used to monitor how often the wearer is speaking. Using one or more microphones, audio received by the wearable device can be analyzed for the presence of speech. In order to maintain privacy, the content of the speech may never be determined, rather only the presence of speech. While the presence of speech may provide a basic indication of social interaction, speech may originate from sources other than the wearer, such as a television. In some embodiments, audio data collected using one or more microphones can be evaluated in combination with data from one or more other sensors, such as a photoplethysmography (PPG) sensor. Data from a PPG sensor may be useful in identifying whether the wearer is the person speaking. Using both data obtained from a PPG sensor and one or more microphones can provide more accurate data of whether the wearer is speaking. Further, additional data may be used to provide a more accurate indication of whether the wearer is speaking and, possibly, whether the wearer is participating in a person-to-person or face-to-face conversation.

Data collected on the wearer speaking and/or person-to-person communications may be used to provide the wearer with metrics, such as the amount of time in a day that the wearer spoke or participated in person-to-person conversations. Using this data, the wearer can better understand the amount of day-to-day social interaction they are getting and whether they should take steps to increase (or perhaps decrease!) their amount of social interaction.

Figure 1:
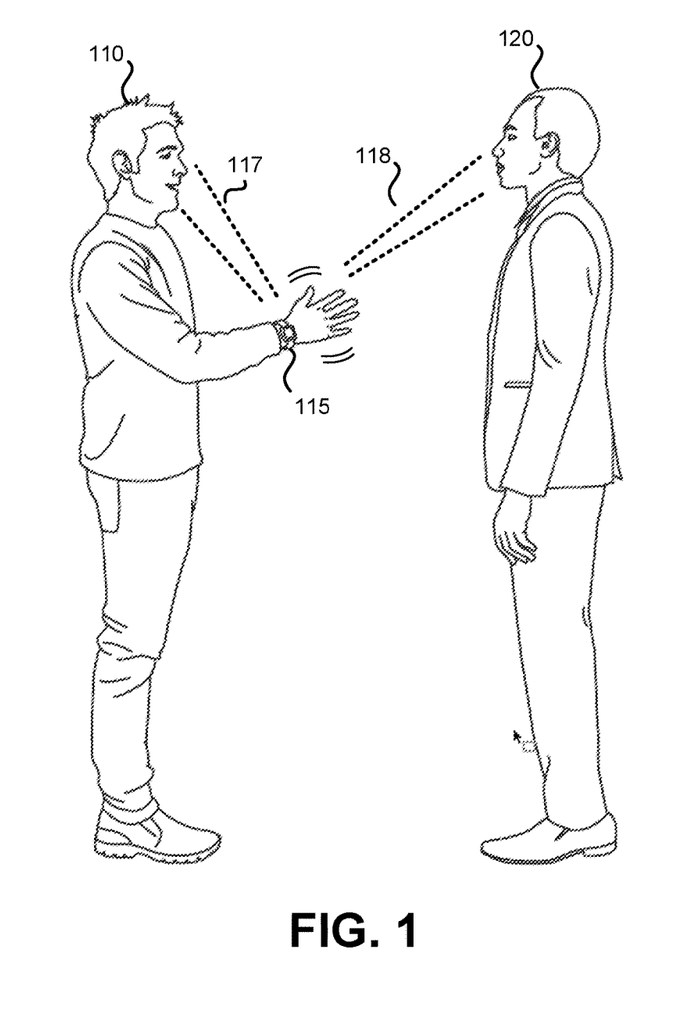
FIG. 1 illustrates an embodiment of a person conducting a face-to-face conversation while wearing a social interaction measurement device.

FIG. 1 illustrates an embodiment 100 of a person 110, also referred to as wearer 110, conducting a face-to-face conversation with person 120 while wearing social interaction measurement device 115 ("SIM device 115"). A face-to-face conversation is defined to be a conversation where the at least two participants are in physical proximity to each other without the use of any electronic devices to relay communications, such as phones, computers, walkie-talkies, etc. For instance, in a typical face-to-face conversation, two people may be within 3 meters (or about 10 feet) of each other.

In FIG. 1, wearer 110 is wearing SIM device 115 on his wrist. In other embodiments, SIM device 115 may be worn by wearer differently, such as in the form of eyeglasses or around the neck of wearer 110; on the chest of wearer 110; on an ankle of wearer 110. Some embodiments of SIM device 115 benefit from direct contact with the skin of wearer 110. For embodiments that do not need direct skin contact, wearer 110 may carry SIM device 115 in their pocket. (While embodiments herein refer to the user as the "wearer," the term should be understood to include embodiments in which the wearer has SIM device 115 with themselves, but is not necessarily wearing SIM device 115. For example, a wearer may have SIM device 115 in a pocket.)

As illustrated in FIG. 1, wearer 110 is talking to person 120. SIM device 115 may capture an audio stream that includes speech by wearer 110 and person 120. In addition to speaking, wearer 110 may gesticulate with his arms, such as raising his arm on which he wears SIM device 115. Additionally or alternatively, such as by using multiple microphones, SIM device 115 can determine a direction from which speech originates. Such a determination can be useful to determine if wearer 110 is speaking to another person or is speaking on the phone or using some other form of electronic device. In the illustrated embodiment, SIM device 115 may sense speech originating from direction 117 and from direction 118. Speech originating from different directions can be indicative of face-to-face communication. Additionally or alternatively, a source separation algorithm can be executed that determines how many speakers are present.

Figure 2:
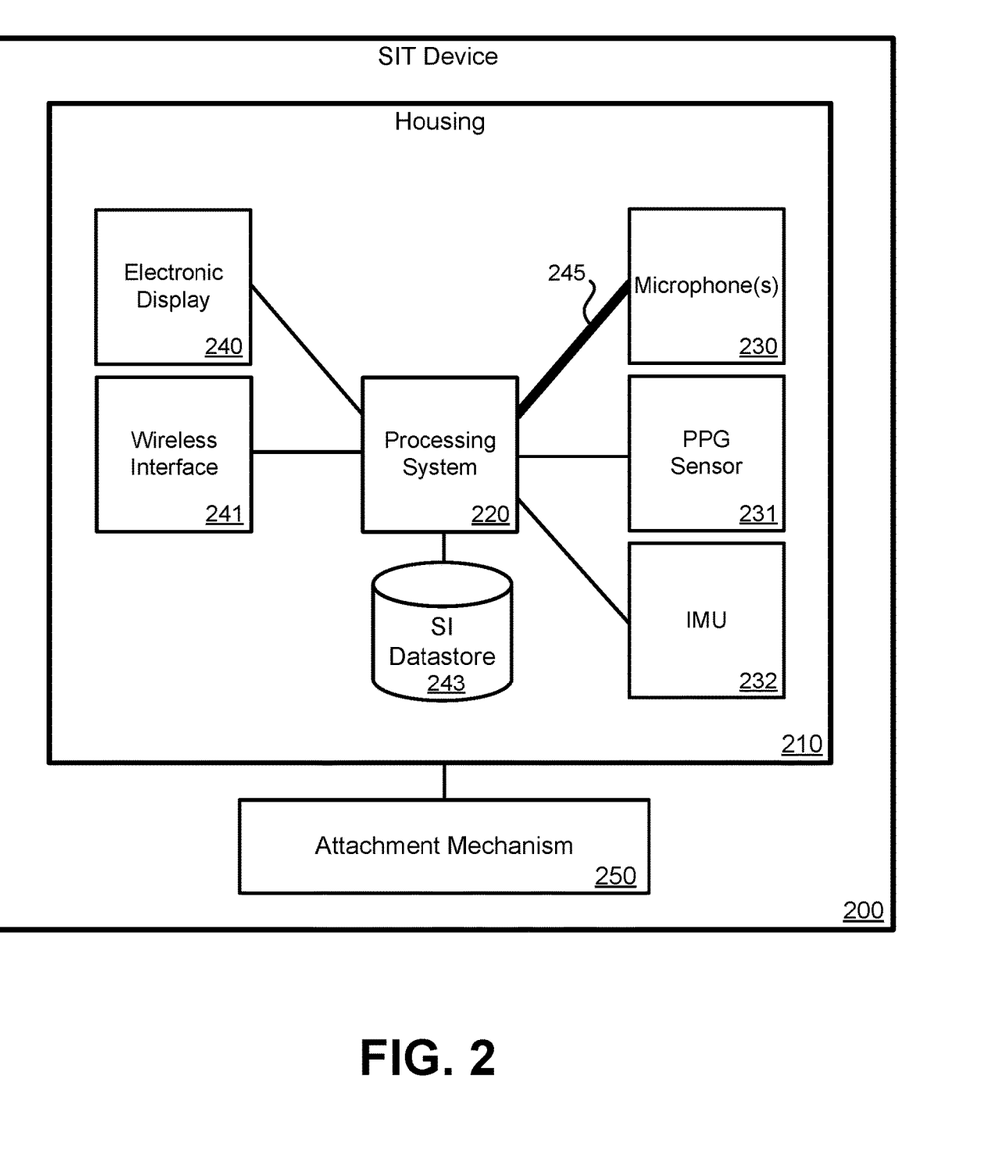
FIG. 2 illustrates an embodiment of a social interaction measurement device.

FIG. 2 illustrates an embodiment of a social interaction measurement device 200 ("SIM device 200"). SIM device 200 can include a housing 210 and attachment mechanism 250. Attachment mechanism 250 can be attached with housing 210 and can help keep SIM device 200 against the skin of the wearer. For example, attachment mechanism 250 can be a wristband, ankle band, lanyard, chest strap, or some other attachment means, such as to hold SIM device 200 around the wearer's neck. In other embodiments, SIM device 200 may not need to be in direct skin contact. In some embodiments, SIM device 200 may be a smartphone, gaming device, or stand-alone device that a user tends to keep with themselves, such as in a pocket.

Housing 210 can house various components of SIM device 200. The housing itself may be made of a rigid or semi-rigid material, such as metal or plastic. Housing 210 may include a transparent portion that allows electronic display 240 to be visible through housing 210. Housing 210 may be permanently or removably attached with attachment mechanism 250.

Components of SIM device 200 that are housed by housing 210 can include: processing system 220; one or more microphones 230; PPG sensor 231; inertial measurement unit (IMU) 232; electronic display 240; wireless interface 241; and social interaction (SI) data store 243. Processing system 220 may include one or more processors, which can include special-purpose or general-purpose processors that execute instructions stored using one or more non-transitory processor readable mediums. Processing system 220 can include one or more processors that are designed to execute machine learning (ML) models. Such processors, while able to analyze whether speech is or is not present, may not be able to analyze the content of such speech. Therefore, privacy of the content of the speech is maintained. Syntiant® Neural Decision Processors™ represent one family of commercial processors that can execute a machine learning model that is trained to determine the presence of speech but otherwise ignore the content of such speech.

One or more microphones 230 may be in communication with processing system 220. If multiple microphones 230 are present, based upon the difference in time of arrival of sound at the multiple microphones, a direction from which a sound, such as speech, originated may be determined in relation to SIM device 200. One or more microphones 230 may be in direct communication with only processing system 220 via direct connection 245. Specifically, one or more microphones 230 can be electrically connected to only a processor that executes a machine learning model that determines (e.g., a binary determination of whether or not speech is determined to be present) or scores (e.g., indicates a likelihood of speech being present) if speech is or is not present. The processor does not have the capability to analyze the content of the speech. In an eyeglass embodiment of a wearable device, one or more bone-conduction microphones may be used.

PPG sensor 231 is in communication with processing system 220. PPG sensor 231 may require direct skin contact with a wearer of SIM device 200. Accordingly, a portion of PPG sensor 231 may reside outside of housing 210 or may otherwise be accessible through housing 210. PPG sensor 231 may generally use light to sense the rate of blood flow as controlled by the wearer's heart's pumping action. When speaking, a wearer's breathing pattern may tend to exhibit particular characteristics, such as a relatively quick intake of air, followed by the slow output of air while speaking compared to breathing when not speaking. This alteration in breathing has a small but measurable effect on the rate of blood flow as measured using a PPG sensor 231. Therefore, PPG data from PPG sensor 231 may be used to determine whether a wearer is speaking.

Notably, PPG data may be less accurate in determining whether a wearer is speaking than a determination made using audio. Therefore, it may not be preferable to use only data captured using PPG sensor 231. Rather, it may be preferable to use data from one or more microphones 230 in combination with data from PPG sensor 231. In some embodiments, data from one or more microphones 230 is used to determine whether speech is present; data from PPG sensor 231 can then be used to determine whether the speech likely originated from the wearer or from some other source.

IMU 232 is in communication with processing system 220. IMU 232 may include an accelerometer, a gyroscope, and/or some other form of inertial measurement system. IMU 232 can be used to determine the orientation of SIM device 200 to the ground based on the acceleration of gravity and can be used to determine movement of SIM device 200.

Wireless interface 241 is in communication with processing system 220 and allows for communication with various wireless networks and/or wireless devices using one or more communication protocols. Wireless interface 241 may allow for communication with a Wi-Fi based wireless local area network. Wireless interface 241 can allow for communication directly with other devices, such as via Bluetooth, Bluetooth Low Energy (BLE), or some other low-power device-to-device communication protocol. In some embodiments, wireless interface 241 allows for communication with a wearer's smartphone, thus allowing information collected using SIM device 200 to be analyzed by and presented using the wearer's smartphone.

In some embodiments, electronic display 240 may be present. Electronic display 240 can allow for information determined based on data collected from the various sensors of SIM device 200 to be directly presented to a user. For instance, electronic display 240 may be able to present text and/or graphical indications of whether the wearer's social interactions are above, at, or below a goal for a specific time period, such as a day.

Processing system 220 may also be in direct communication with SI data store 243. SI data store 243 may be used to store statistics about a wearer's social interactions over time. When processing system 220 determines that the social interaction is occurring, information indicative of the duration of time of the social interaction may be stored to SI data store 243. At a later time, the information indicative of the duration of time of various social interactions may be aggregated by processing system 224 output either directly to the user via electronic display 240 or via wireless interface 241 for presentation remotely, such as on a smartphone or other form of mobile device. Additionally or alternatively, the information indicative of the duration of time various social interactions may be transmitted to a remote device or system, such as a cloud-based server, for analysis, storage, and/or output to the wearer.

Figure 3:
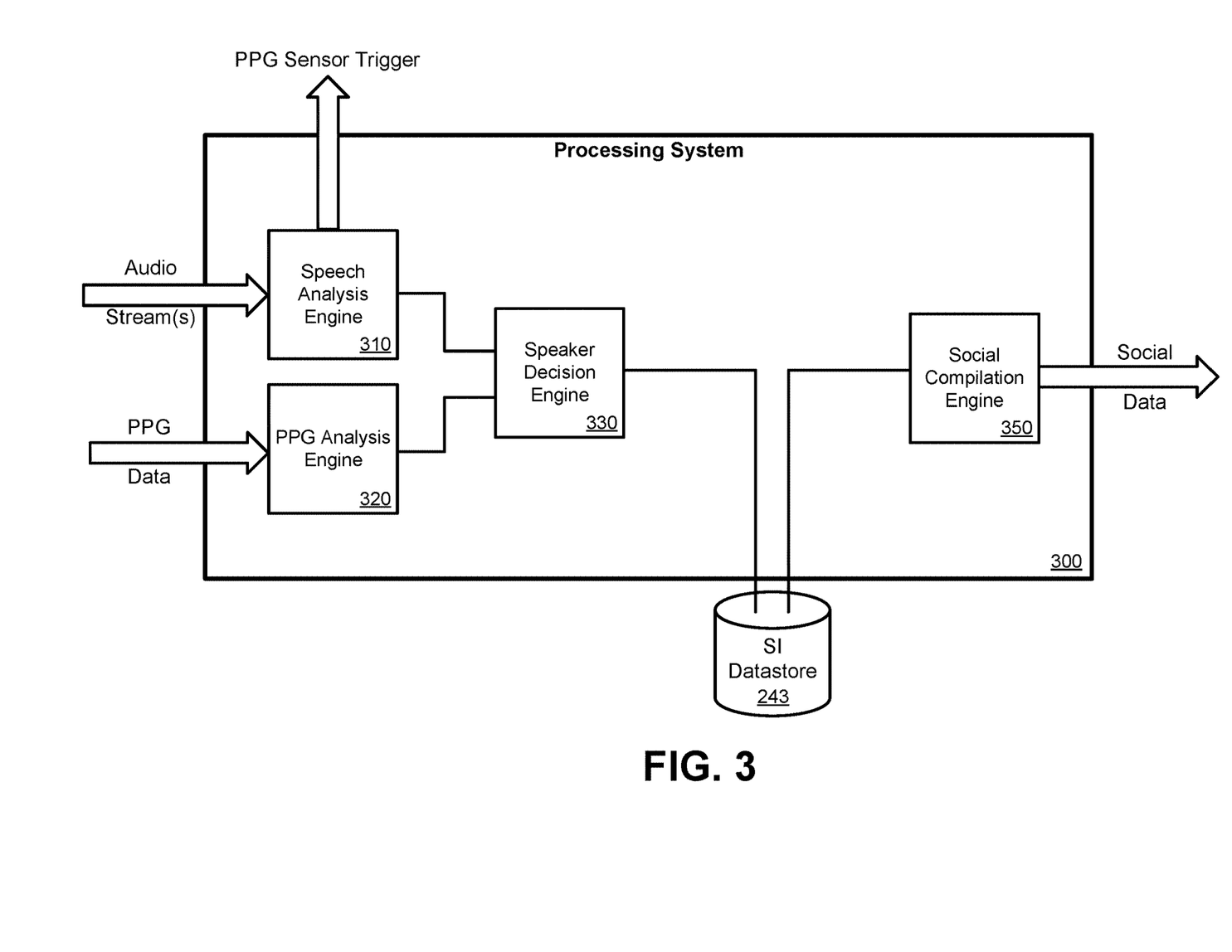
FIG. 3 illustrates an embodiment of a processing system for a social interaction measurement device.
Figure 4:
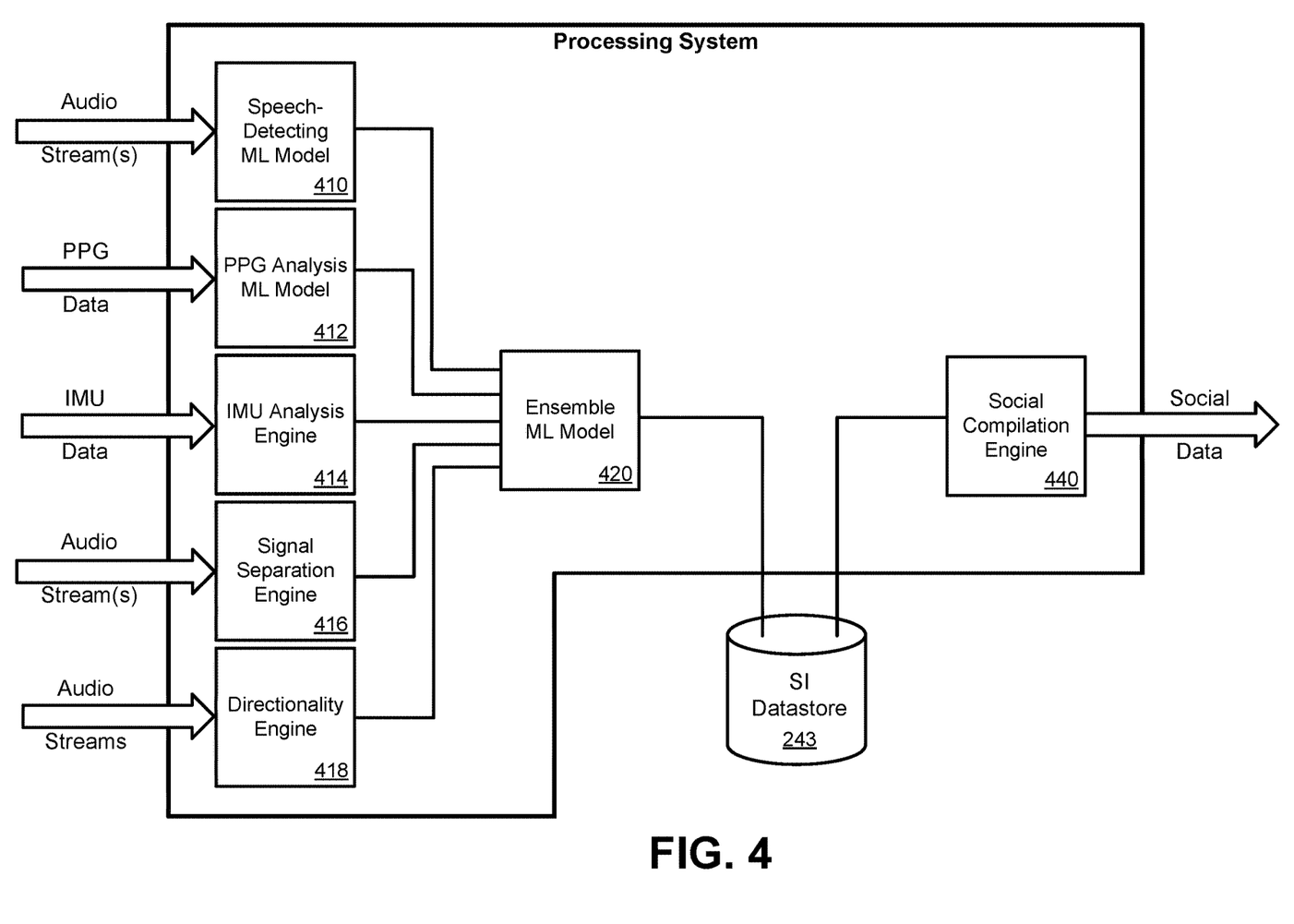
FIG. 4 illustrates another embodiment of a processing system for a social interaction measurement device.

FIGS. 3 and 4 represent various embodiments of processes or components that can be implemented using one or more processors in order to analyze data obtained from the various sensors and components detailed in relation to FIG. 2. FIG. 3 illustrates an embodiment of processing system 300 for a social interaction measurement device. Processing system 300 represents an embodiment of processing system 220 of FIG. 2.

Processing system 300 comprises: speech analysis engine 310; PPG analysis engine 320; speaker decision engine 330; and social compilation engine 350. Speech analysis engine 310 can receive one or more audio streams from the one or more microphones of SIM device 200. One audio stream may be present for each microphone of SIM device 200. Speech analysis engine 310 may be a machine learning (ML) model, such as a neural network, that has been trained to detect whether or not speech is present within the one or more audio streams. More specifically, a set of training data may have been created that includes a large number of audio clips, some of which include speech and some of which do not include speech. Each of these audio clips may be truth tagged to indicate whether or not speech is or is not actually present. This training set of data may then be used to train a machine learning model that receives one or more audio streams and outputs either a binary indication of whether speech is present or a score indicative of the likelihood that speech is present. Notably, the ML model does not analyze the content of the speech. An output of the indication of whether speech is present or the score that is indicative of the likelihood that speech is present may be output to a speaker decision engine 330.

The various machine learning models implemented herein can be implemented in varying forms, involving supervised, semi-supervised, unsupervised, and reinforcement learning. Other than neural networks, other forms classification-based supervised machine learning can be applied, such as trees, logistic regression, Naïve-Bayes, and Support Vector Machines (SVM).

In some embodiments, so as to save power, not all sensors or engines executed by processing system 300 may operate continuously. Rather, one or more conditions may need to be satisfied first. In some embodiments, speech analysis engine 310 may be required to determine that speech is likely present in order for analysis or even sensing of PPG data to begin. Speech analysis engine 310 may serve as a trigger to activate PPG sensor 231 and/or activate PPG analysis engine 320.

PPG analysis engine 320 may receive a stream of PPG data and output either a binary indication or a score indicative of whether the PPG data is indicative of the wearer speaking or not. PPG analysis engine 320 may be an ML model, such as a neural network, that has been trained to detect whether or not speech is present within the PPG data stream. More specifically, a set of training data may have been created that includes a large number of samples of PPG data, some of which were captured when the subject was speaking and some of which were captured when the subject was not speaking. Each of these samples of PPG data may be truth tagged to indicate whether or not speech was actually present when the PPG measurements of the blood flow were taken. The alterations in breathing caused by the presence or absence of speech are evident in the PPG blood flow measurements. This training set of data may then be used to create an ML model that receives a PPG data stream as an input and outputs either a binary indication of whether the wearer is determined to be speaking or a score indicative of the likelihood that the wearer of the device is speaking.

Speaker decision engine 330 can serve to use information from speech analysis engine 310 and PPG analysis engine 320 to determine whether the wearer of the SIM device is speaking. Speaker decision engine 330 may analyze the output of speech analysis engine 310 to determine that speech is present. If speech is determined to be present and PPG analysis engine 320 indicates that some of the speech originated from the wearer but other speech did not originate from the wearer (e.g., PPG data is not indicative of speech but the audio is indicative of speech), speaker decision engine 330 can determine that a face-to-face (or at least a person-to-person) conversation is occurring. While such a decision may not be perfect, for example it may capture a wearer using a speakerphone to talk to someone else, it may be acceptable that such communication is also considered, if not a face-to-face conversation, at least a social interaction. For example, speaker decision engine 330 may determine whether a defined percentage range of the detected speech is attributed to the wearer, such as between 20% and 80% of speech. In other embodiments, such as detailed in relation to ensemble ML model 420 of FIG. 4, a second-level ML model may be used to determine the type of communication occurring.

In some embodiments, PPG data may not be used. For example, an embodiment implemented on a smartphone or a simple wearable design may use only audio data. Such embodiments may use an output of speech analysis engine 310 to determine whether or not the user/wearer is speaking. Some such embodiments may not be able to distinguish between background speech and the wearer's speech or, in some embodiment, speech analysis engine 310 may be trained to specifically detect speech of the user/wearer. Other embodiments may be able to distinguish whether or not the user/wearer is speaking using other measurements, such as the direction from which speech originated and/or a source separation algorithm.

The output of speaker decision engine 330 may be stored by SI data store 243. The information stored to SI data store 243 may indicate whether or not a social interaction, such as a face-to-face conversation, has occurred and a duration of the social interaction. Social compilation engine 350 may access SI data store 243 to analyze social interactions for a particular time period, such as a particular day. The output of social compilation engine 350 may be an indication of the number and/or duration of social interactions held by the wearer in a given day or some other time period. In some embodiments, a comparison with a predefined goal value may be provided, such as a system or user-defined goal value of how much social interaction the user/wearer should try to have in a given time period (e.g., per day). The output of social compilation engine 350 may be transmitted to another device, such as to a smart phone or cloud-based server system, and/or may be output for presentation to the wearer via electronic display of the SIM device.

FIG. 4 illustrates an embodiment of processing system 400 for a social interaction measurement device. Processing system 400 can represent a more advanced embodiment of processing system 300, which can also function as processing system 220 of FIG. 2. Processing system 400 can comprise: speech-detecting ML model 410; PPG analysis ML model 412; IMU analysis engine 414; signal separation engine 416; directionality engine 418; ensemble ML model 420; and social compilation engine 440.

Speech-detecting ML model 410 may receive one or more audio streams and determine whether or not speech is present. Speech-detecting ML model 410 may function as detailed in relation to the ML model of speech analysis engine 310 of FIG. 3. In some embodiments, sound pressure level (SPL) may be used to determine whether or not speech is likely present. If a wearer is speaking intermittently, the measured SPL may vary significantly. Speech-detection ML model 410 may be trained to perform its classification based at least in part on SPL. Alternatively, a separate algorithm or ML model, referred to as SPL analysis algorithm may be used to determine whether speech is present or likely present based on SPL data. PPG analysis ML model 412 may function as detailed in relation to the ML model of PPG analysis engine 320. PPG analysis ML model 412 and/or activation of the PPG sensor may be contingent on speech-detecting ML model 410 identifying that speech is present.

IMU analysis engine 414 may receive a stream of IMU data from an IMU sensor such as an accelerometer and output either a binary indication or a score indicative of whether the PPG data is indicative of the wearer speaking or not. IMU analysis engine 414 may be an ML model, such as a neural network, that has been trained to detect whether or not speech is present based on the IMU data stream. More specifically, a set of training data may have been created that includes a large number of samples of IMU data, some of which were captured when the subject was speaking and some of which were captured when the subject was not speaking. Each of these IMU data samples may be truth tagged to indicate whether or not speech was actually present when the IMU data samples were captured. This training set of data may then be used to train an ML model that receives an IMU data stream as an input and outputs either a binary indication of whether the wearer is speaking or a score indicative of the likelihood that the wearer is speaking.

In some embodiments, the data from an IMU sensor may be particularly useful in identifying whether the wearer is asleep. IMU analysis engine 414 may be used to output an indication of whether the wearer is asleep. If the wearer is determined to be asleep, any determination of the wearer participating in speech may be classified as a false positive. Therefore, IMU data being indicative of the wearer being awake may be a necessary condition for the wearer to be determined to be participating in a person-to-person or face-to-face conversation.

Signal separation engine 416 can determine the number of source signals from a set of mixed signals without the aid of information, or with little information, about the source signals or the mixing process. Namely, in the field of audio, such signal separation can be referred to as the "cocktail party problem." Signal separation engine 416 can receive audio streams from multiple microphones and can output an indication of the number of audio sources determined to be present. To perform this determination, signal separation engine 416 can use methods such as: principal components analysis; singular value decomposition; independent component analysis; dependent component analysis; non-negative matrix factorization; low-complexity coding and decoding; stationary subspace analysis; or common spatial pattern.

Directionality engine 418 may be present in some embodiments. Directionality engine 418 can analyze multiple audio streams to determine the direction sound or, more specifically, speech originated from. Referring to FIG. 1, determining the direction from which speech originated may be important in determining whether a wearer is talking to another person. The exact direction determined may be less important than determining that speech is originating from two or more directions. If speech is determined to be present in an audio stream and the speech originated from direction 117, this may be indicative that the wearer is speaking. If speech is determined to be present in an audio stream and the speech originated from direction 118, this may be indicative that speech is originated from someone or something other than wearer 110. If speech alternates between direction 117 and direction 118, this may be indicative that a conversation is occurring. The output of directionality engine 418 may be an indication of whether audio or speech originates from one or more than one direction.

Directionality engine 418 may receive multiple audio streams from multiple microphones and output either a binary indication or a score indicative of whether the audio streams are indicative of audio (or specifically speech) originating from multiple sources. Directionality engine 418 may be an ML model, such as a neural network, that has been trained to detect whether or not audio originating from multiple sources is present. More specifically, a set of training data may have been created that includes a large number of samples of audio streams, some of which were captured from a single source and others from multiple sources. Each of these audio clips may be truth tagged to indicate the actual number of sources of the sound data. This training set of data may then be used to create an ML model that receives multiple audio streams as inputs and outputs either a binary indication of whether multiple sources of sound (or speech) are present or not (or, in some embodiments, the specific number of detected sources of sound or speech. In some embodiments, directionality engine 418 is activated based on the presence of speech as determined by speech-detecting ML model 410. In such embodiments, if speech is present, directionality engine 418 is executed; if not, directionality engine 418 is not executed.

Ensemble ML model 420 can represent a second-level ML model in that it uses the output of other ML models (and possibly other sources) as an input. Ensemble ML model 420 can use the output of speech-detecting ML model 410, PPG analysis ML model 412, IMU analysis engine 414, signal separation engine 416, and/or directionality engine 418 as inputs. In some embodiments, ensemble ML model 420 makes a binary classification, such as whether or not a face-to-face (or at least person-to-person) social interaction is occurring. In other embodiments, ensemble ML model 420 can make a classification into multiple possible classes, such as: face-to-face social interaction; electronic social interaction (e.g., via phone, video conference, etc.); or no social interaction.

Ensemble ML model 420 may receive a stream of data from speech-detecting ML model 410, PPG analysis ML model 412, IMU analysis engine 414, signal separation engine 416, and/or directionality engine 418. In some embodiments, ensemble ML model 420 may require that speech-detecting ML model 410 identify the presence of speech before ensemble ML model 420 is executed.

Ensemble ML model 420 may be an ML model, such as a neural network, that has been trained to detect whether or not a social interaction is present based on outputs from multiple other components that include other ML models. More specifically, a set of training data may have been created that includes a large number of samples of outputs from speech-detecting ML model 410, PPG analysis ML model 412, IMU analysis engine 414, signal separation engine 416, and/or directionality engine 418, some of which were captured when the subject was performing social interactions and some of which were captured when the subject was not participating in a social interaction. Each of these instances of training data may be truth tagged to indicate whether or not a social interaction was or was not actually being performed when the data was collected. This training set of data may then be used to create a "second level" ML model that serves to classify a social interaction of the wearer based on the output of various other models, algorithms, and/or engines. The output of the ensemble ML model 420 may be a binary indication of whether a social interaction is occurring, a classification of a type of social interaction occurring, or a score indicative of the likelihood that a social interaction is occurring. If the output is a classification of a type of social interaction, the types may be selected from: face-to-face social interaction; person-to-person social interaction (e.g., an electronic social interaction via video conference or phone call); a video game social interaction; or being solitary.

The output of ensemble ML model 420 may be stored by SI data store 243. The information stored to SI data store 243 may indicate whether or not a social interaction or a type of social interaction has occurred and a duration of the social interaction. Social compilation engine 440 may access SI data store 243 to analyze social interactions for a particular time period, such as a particular day, week, or month. The output of social compilation engine 350 may be an indication of the total number and/or duration of social interactions held by the wearer in a given day or some other time period. In some embodiments, a comparison with a predefined goal value may be provided, such as a system or wearer-defined goal value of how much social interaction the wearer should try to have in a given time period (e.g., per day). The output of social compilation engine 350 may be transmitted to another device, such as to a smart phone or cloud-based server system, and/or may be output for presentation to the wearer via electronic display of the SIM device.

Figure 5:
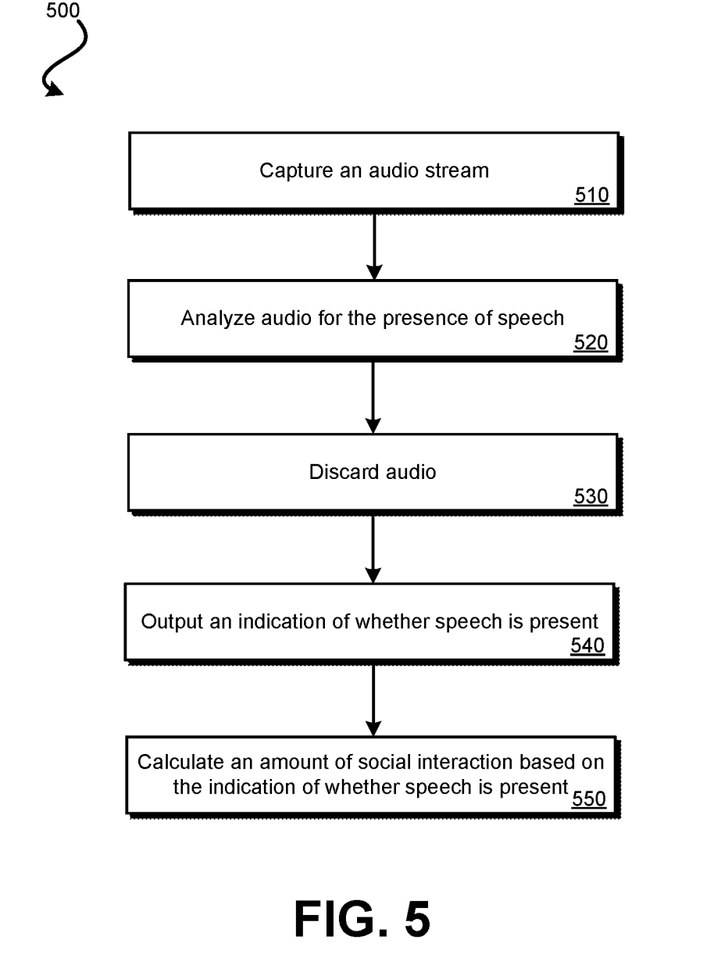
FIG. 5 illustrates an embodiment of a method for social interaction measurement.
Figure 6:
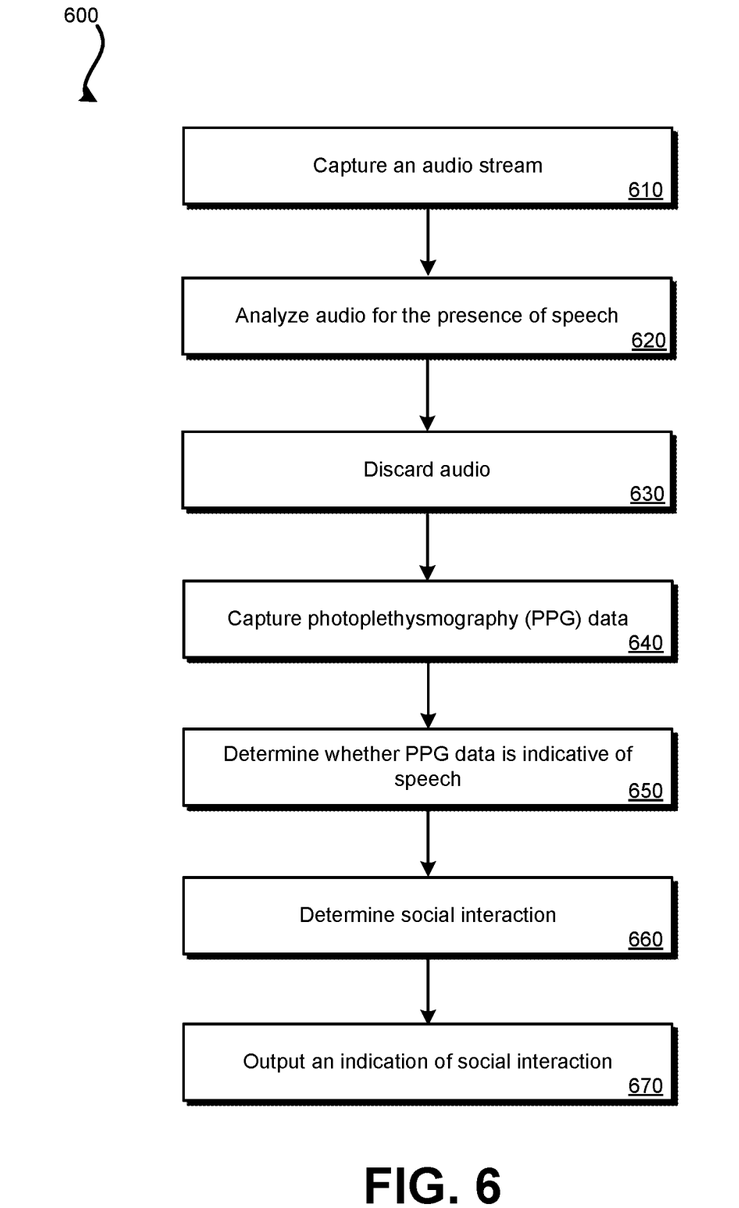
FIG. 6 illustrates another embodiment of a method for social interaction measurement.
Figure 7:
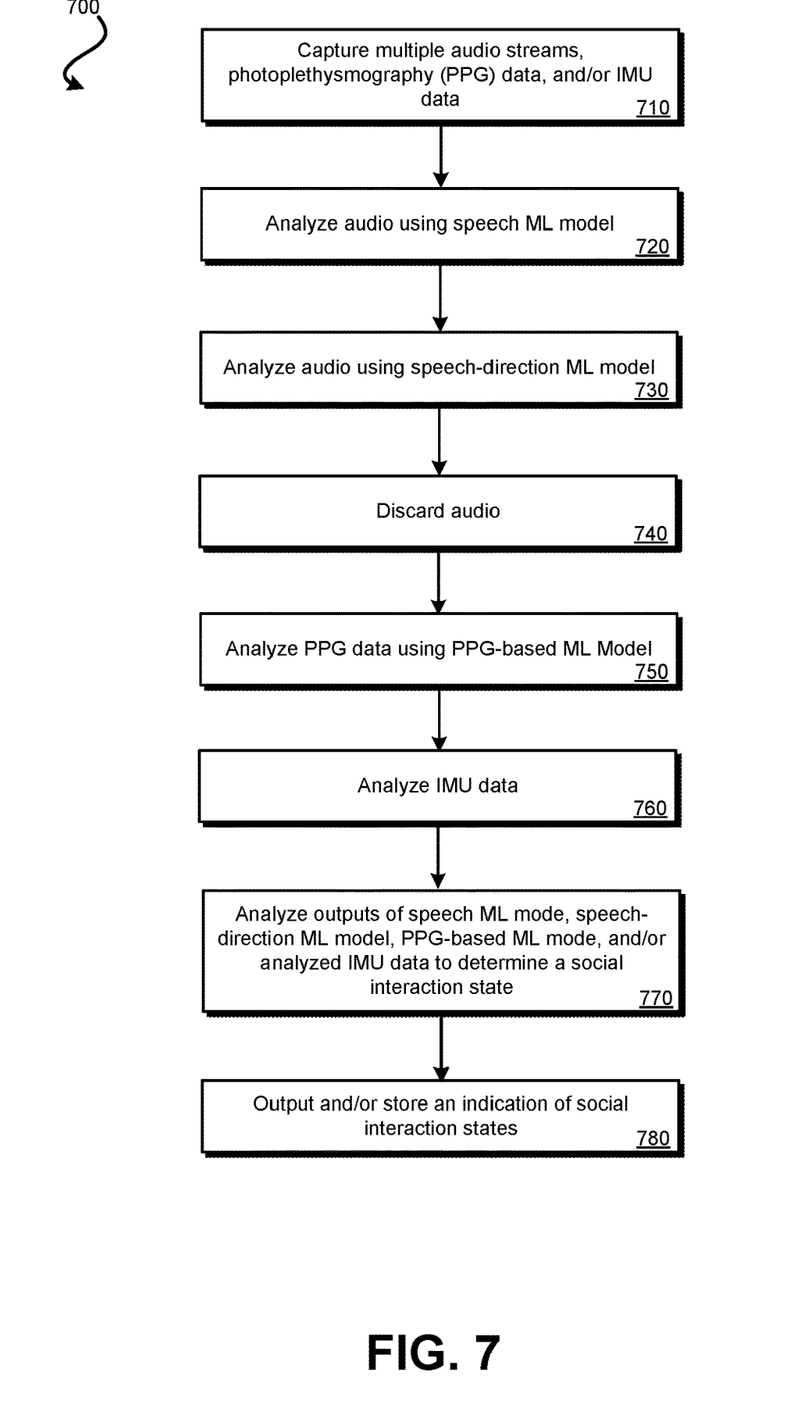
FIG. 7 illustrates an embodiment of a method for face-to-face social interaction measurement.

Various methods may be performed using the devices and systems detailed in relation to FIGS. 1-4. FIGS. 5-7 represent methods of increasing complexity that can be used to determine whether a social interaction has occurred, while maintaining the privacy of the wearer. FIG. 5 illustrates an embodiment of a method 500 for social interaction measurement. Method 500 may be performed by a device that measures an amount of speech, but does not monitor the content of speech.

At block 510, an audio stream may be captured using one or more microphones. At block 520, the audio stream may be analyzed for the presence of speech. A machine learning model may be used to analyze the audio stream, the ML model having been trained to detect the presence of speech but not analyze the content of the speech. Once the speech has been analyzed at block 520, the audio may be discarded 530 or otherwise not saved or stored.

In some embodiments, a multi-stage approach may be taken in which a single stream of audio from a microphone is initially analyzed. If speech is determined to be present in the single stream, audio captured from additional microphones is analyzed and/or one or more multiple other models or components are used to analyze the audio stream. In such embodiments, rather than deleting or discarding audio data immediately after the analysis of block 520, audio data may be buffered for a period of time, such as 1-5 seconds. This buffering can allow for a determination to be made as to whether other buffered audio streams and/or the audio stream should be analyzed using other models or components should be analyzed.

At block 540, based on the analysis of block 520, an indication of whether or not speech is present may be output. The presence of speech may serve as the basis for whether a social interaction is occurring. Therefore, in this embodiment, if speech is detected, it is assumed that the wearer of the device is speaking and that that speech is sufficient to qualify as a social interaction.

At block 550, the amount of social interaction of the wearer is calculated based on the output of block 540. The output of block 540 may be aggregated over a period of time, such as an hour, a day, week, or month to provide an indication of the aggregate amount of social interaction of the wearer over that period of time. In some embodiments, this value is compared and contrasted with a goal value for the wearer.

FIG. 6 illustrates another embodiment of a method 600 for social interaction measurement. Method 600 may be performed by a device that measures speech in multiple ways, but does not monitor the content of speech. At block 610, one or more audio streams may be captured using one or more microphones. At block 620, the audio stream may be analyzed for the presence of speech. A machine learning model may be used to analyze the one or more audio streams, the ML model having been trained to detect the presence of speech but not analyze the content of the speech. Once the speech has been analyzed at block 630, the audio may be discarded or otherwise not saved or stored.

At block 640, PPG data may be captured using a PPG sensor. In some embodiments, PPG data may be continuously captured; in other embodiments, PPG data may only be captured if the analysis of block 620 is indicative of speech being present. Having block 640 contingent on block 620 may help save power by not having the PPG sensor operating unless necessary. While block 620 may be particularly accurate in determining whether speech is present, PPG data may be particularly useful for determining if the wearer of the SIM device is speaking. At block 650, the PPG data may be analyzed, such as by using an ML model, to determine if speech is present. If speech is determined to be present based on PPG data, since PPG data is measured using blood flow, it is now known that the speech belongs to the wearer of the SIM device.

At block 660, a determination of whether the wearer is participating in a social interaction may be based on the output of block 620 and block 650. In some embodiments, determining that the social interaction is present is based on a series of hard rules such as comparing an amount of time during which the wearer is speaking and not speaking when the audio is indicative of speech being present. That is, a person-to-person or face-to-face social interaction may be defined as when speech is present and between 20% and 80% of the speech is attributed to the wearer. In other embodiments, rather than using hard rules, a machine learning model is trained and applied to analyze the output of blocks 620 and 650 to determine if a social interaction is present. In some embodiments, multiple classifications of social interactions are possible including face-to-face and electronic.

At block 670, the amount of social interaction of the wearer is calculated based on the output of block 660. The output of block 660 may be aggregated over a period of time, such as an hour, a day, week, or month to provide an indication of the aggregate amount of social interaction of the wearer over that period of time. In some embodiments, this value is compared and contrasted with a goal value for the wearer.

FIG. 7 illustrates an embodiment of a method 700 for face-to-face social interaction measurement. Method 700 may be performed by a device, such as SIM device 115, that measures speech and wearer activity in multiple ways but does not monitor the content of speech.

At block 710, multiple audio streams may be captured using one or more microphones, PPG data can be captured using a PPG sensor, and/or IMU data may be captured using an accelerometer or some other form of IMU. At block 720, the audio stream may be analyzed for the presence of speech. An ML model may be used to analyze the one or more audio streams, the ML model having been trained to detect the presence of speech but not analyze the content of the speech. In some embodiments, some sensor data, such as PPG data, is only collected if speech is identified at block 720.

At block 730, the audio may further be analyzed to determine a direction from which the audio or specifically the speech within the audio streams originated. The output of block 730 may be a determination that audio or speech originated from at least two different directions. Once the audio has been analyzed at blocks 720 and 730, the audio may be discarded or otherwise not saved or stored at block 740.

At block 750, the PPG data may be analyzed, such as by using an ML model, to determine if speech is present. If speech is determined to be present based on PPG data, since PPG data is measured using blood flow of the wearer of the PPG sensor, it is known that the speech belongs to the wearer of the SIM device (and not someone else in the vicinity or some electronic device).

At block 760, IMU data captured using the IMU sensor may be analyzed. Various movements of the wearer may be indicative of whether the wearer is sleeping, or even possibly speaking, such as wearer 110 gesticulating in FIG. 1. IMU data may be analyzed, possibly using an ML model to determine a wearer state, such as selected from: asleep, awake and not speaking, awake and speaking. In some embodiments, if the IMU data is indicative of the wearer being asleep, data from other sensors may be discarded and assumed to be false positives.

At block 770, another ML model, which can be referred to as an ensemble ML model, may analyze the output of the speech ML model, the speech-direction ML model, and/or the analyzed IMU data. This ensemble ML model may be trained to identify a social interaction state of the wearer based on the inputs. The ensemble ML model may output a classification of: no social interaction, person-to-person (or face-to-face) interaction; or electronic person-to-person interaction. In other embodiments, the ensemble ML model may output a classification of: no social interaction; or person-to-person social interaction. The classifications and times associated with the classifications may be stored locally, such as in SI datastore or remotely in the cloud. In some embodiments, additionally or alternatively, a signal separation algorithm may be used to analyze the audio streams from multiple microphones. This analysis may determine the number of signal sources (e.g., people speaking) for the captured audio streams. In some embodiments, the output of the signal separation algorithm may be further used in performing the analysis of block 770.

At block 780, the amount of social interaction of the wearer is calculated based on the output of block 770. The output of block 660 may be aggregated over a period of time, such as an hour, a day, week, or month, to provide an indication of the aggregate amount of social interaction of the wearer over that period of time. In some embodiments, this value is compared and contrasted with a goal value for the wearer. The wearer may be given reminders to reach out to someone if a significant amount of time passes without the wearer having a social interaction.

It should be noted that the methods, systems, and devices discussed above are intended merely to be examples. It must be stressed that various embodiments may omit, substitute, or add various procedures or components as appropriate. For instance, it should be appreciated that, in alternative embodiments, the methods may be performed in an order different from that described, and that various steps may be added, omitted, or combined. Also, features described with respect to certain embodiments may be combined in various other embodiments. Different aspects and elements of the embodiments may be combined in a similar manner. Also, it should be emphasized that technology evolves and, thus, many of the elements are examples and should not be interpreted to limit the scope of the invention.

Specific details are given in the description to provide a thorough understanding of the embodiments. However, it will be understood by one of ordinary skill in the art that the embodiments may be practiced without these specific details. For example, well-known, processes, structures, and techniques have been shown without unnecessary detail in order to avoid obscuring the embodiments. This description provides example embodiments only, and is not intended to limit the scope, applicability, or configuration of the invention. Rather, the preceding description of the embodiments will provide those skilled in the art with an enabling description for implementing embodiments of the invention. Various changes may be made in the function and arrangement of elements without departing from the spirit and scope of the invention.

Also, it is noted that the embodiments may be described as a process which is depicted as a flow diagram or block diagram. Although each may describe the operations as a sequential process, many of the operations can be performed in parallel or concurrently. In addition, the order of the operations may be rearranged. A process may have additional steps not included in the figure.

Having described several embodiments, it will be recognized by those of skill in the art that various modifications, alternative constructions, and equivalents may be used without departing from the spirit of the invention. For example, the above elements may merely be a component of a larger system, wherein other rules may take precedence over or otherwise modify the application of the invention. Also, a number of steps may be undertaken before, during, or after the above elements are considered. Accordingly, the above description should not be taken as limiting the scope of the invention.

What is claimed is:

1. A wearable device, comprising:
   a housing;
   an attachment mechanism, attached with the housing, that permits the wearable device to be worn by a wearer;
   a microphone housed by the housing;
   a photoplethysmography (PPG) sensor, housed by the housing; and
   a processing system comprising at least one processor, communicatively coupled with the microphone and housed by the housing, wherein the processing system is configured to:
   receive an audio signal from the microphone;
   receive a PPG signal from the PPG sensor;
   process the audio signal using an audio-based machine learning model stored by the processing system, wherein the audio-based machine learning model is
trained to detect a presence of speech;
process the PPG signal received from the PPG sensor
using a PPG-based machine learning model stored
by the processing system;
using a first output of the audio-based machine learning
model and a second output of the PPG-based
machine learning model, determine whether the
audio signal comprises speech spoken by the wearer
of the wearable device;
output an indication of whether speech spoken by the
wearer is present within the audio signal based at
least in part on processing the audio signal using the
audio-based machine learning model; and
discard the audio signal such that the audio signal is not
stored after the indication of whether speech is
present is output.

2. The wearable device of claim 1, wherein the processing system is further configured to:
process the first output of the audio-based machine learning model and the second output of the PPG-based machine learning model using a second-level machine learning model, wherein the second-level machine learning model outputs the indication of whether speech is present, wherein:
the indication of whether speech is present is indicative of whether speech spoken by the wearer is present.

3. The wearable device of claim 2, further comprising a plurality of microphones, that comprises the microphone, in communication with the processing system; and
the processing system is further configured to:
process a plurality of audio streams from the plurality of microphones using a directionality analyzer, wherein:
the second-level machine learning model further uses a third output from the directionality analyzer; and
the indication of whether speech is present is further indicative of whether the wearer is participating in a person-to-person conversation.

4. The wearable device of claim 1, further comprising:
an inertial measurement unit (IMU), housed by the housing and in communication with the processing system, that outputs an inertial signal to the processing system, wherein the processing system is further configured to:
process the inertial signal received from the IMU using an inertial-based machine learning model stored by the processing system; and
using the first output of the audio-based machine learning model, the second output of the PPG-based machine learning model, and a third output of the inertial-based machine learning model, determine whether the audio signal comprises speech spoken by the wearer of the wearable device.

5. The wearable device of claim 1, wherein the attachment mechanism comprises a band that permits the wearable device to be worn on a wrist of the wearer.

6. The wearable device of claim 5, wherein the wearable device is a smartwatch that further comprises:
a graphical electronic display, housed by the housing and in communication with the processing system; and
a wireless communication interface, housed by the housing and in communication with the processing system that enables the processing system to communicate wirelessly with a smartphone.

7. The wearable device of claim 1, wherein the processing system is further configured to:
calculate an amount of time in a day that the wearer is socially engaged based at least on the indication of whether speech is present within the audio signal; and
cause the amount of time in the day that the wearer is socially engaged to be output to the wearer.

8. The wearable device of claim 1, wherein the audio signal from the microphone is only input to the audio-based machine learning model.

9. The wearable device of claim 1, wherein the processing system is further configured to:
perform a signal separation analysis on a plurality of audio signals received from a plurality of microphones of the wearable device, wherein an output of the signal separation analysis is an indication of a number of audio sources.

10. A method for social interaction measurement, the method comprising:
capturing, by a microphone of a wearable device, an audio signal;
capturing photoplethysmography (PPG) data using a PPG sensor of the wearable device;
processing, by a processing system of the wearable device, the audio signal using an audio-based machine learning model, wherein the audio-based machine learning model is trained to detect a presence of speech;
processing the PPG data received from the PPG sensor using a PPG-based machine learning model stored by the processing system, wherein the PPG-based machine learning model is trained to detect the presence of speech based on the PPG data;
discarding, by the wearable device, the audio signal such that content of the audio signal is not stored after the audio signal is processed using the audio-based machine learning model;
using a first output of the audio-based machine learning model and a second output of the PPG-based machine learning model, determine whether the audio signal comprises speech spoken by a wearer of the wearable device; and
outputting, by the processing system, an indication of whether speech by the wearer is present within the audio signal based at least in part on processing the audio signal using the audio-based machine learning model.

11. The method for social interaction measurement of claim 10, further comprising:
processing the first output of the audio-based machine learning model and the second output of the PPG-based machine learning model using a second-level machine learning model, wherein the second-level machine learning model outputs the indication of whether speech is present.

12. The method for social interaction measurement of claim 11, further comprising:
wherein capturing the audio signal comprises capturing a plurality of audio signals using a plurality of microphones of the wearable device.

13. The method for social interaction measurement of claim 12, further comprising:
performing a signal separation analysis on the plurality of audio signals received from the plurality of microphones of the wearable device, wherein an output of the signal separation analysis is an indication of a number of audio sources.

14. The method for social interaction measurement of claim 12, further comprising:

processing a plurality of audio streams from the plurality of microphones using a directionality analyzer, wherein:
the second-level machine learning model further uses a third output from the directionality analyzer; and
the indication of whether speech is present is further indicative of whether the wearer is participating in a face-to-face conversation.

\* \* \* \* \*